United States Patent [19]

Klemke

[11] Patent Number: 5,496,806
[45] Date of Patent: Mar. 5, 1996

US005496806A

[54] GLYCOSIDE COMPOUNDS AND PRODUCTION AND USE THEREOF

[75] Inventor: R. Erich Klemke, D-78247 Hilzingen, Germany

[73] Assignee: R. Erich Klemke, Germany

[21] Appl. No.: 239,373

[22] Filed: May 6, 1994

Related U.S. Application Data

[60] Division of Ser. No. 6,447, Jan. 21, 1993, abandoned, which is a continuation-in-part of Ser. No. 815,691, Jan. 24, 1992, abandoned, which is a continuation-in-part of Ser. No. 733,915, Jul. 22, 1991, abandoned, which is a continuation-in-part of Ser. No. 644,002, Jan. 22, 1991, Pat. No. 5,278,296.

[30] Foreign Application Priority Data

Jan. 23, 1990 [DE] Germany .......................... 40 01 895.4

[51] Int. Cl.$^6$ .................. A61K 31/705; C07J 9/00
[52] U.S. Cl. .................. 514/26; 514/885; 514/886; 536/5; 536/18.5; 536/18.6
[58] Field of Search .................. 514/26, 885, 886; 536/5, 18.5, 18.6, 120

[56] References Cited

U.S. PATENT DOCUMENTS

| | | | |
|---|---|---|---|
| 3,642,770 | 2/1972 | Stache et al. | 260/210.5 |
| 3,838,146 | 9/1974 | Stache et al. | 260/210.5 |
| 3,857,832 | 12/1974 | Hartenstein et al. | 260/210.5 |
| 3,859,047 | 1/1975 | Klein | 23/230 B |
| 3,904,599 | 9/1975 | Stache et al. | 260/210.5 |
| 3,950,323 | 4/1976 | Stache et al. | 260/210.5 |
| 3,953,422 | 4/1976 | Pfeiffer | 260/210 R |
| 4,157,391 | 6/1979 | Kilame et al. | 424/238 |
| 4,304,726 | 12/1981 | Arakawa et al. | 260/397.2 |
| 4,402,948 | 9/1983 | Matsumura | 424/182 |
| 5,278,296 | 1/1994 | Klemke | 536/5 |

FOREIGN PATENT DOCUMENTS

| | | |
|---|---|---|
| 2007410 | 1/1970 | France . |
| 3127933 | 8/1982 | Germany . |

OTHER PUBLICATIONS

Ferrier, *J. Chem. Soc.* (1962), "The Reaction Between 3,4,6–Tri–O–Acetyl–D–Glucal and p–Nitrophenol," 3667–3670.

Ferrier, "Unsaturated Sugars," *Adv. Carbohydrate Chemistry*, 20, pp. 90–91 (1965).

Ferrier, J. Chem. Soc., (1969) "Unsaturated Carbohydrates," 570–575.

Honda, Carbohydrate Research, 29 (1973), "Preparation of O–(2–deoxy–α–D–arabino–hexopyranosyl)–(1–6)–D–glucose by oxyiodination–hydrogenation method", pp. 488–491.

Garegg, Carbohydrate Research, 92 (1981), "Novel Glycosylation Reagents: synthesis of disaccharides containing 2–deoxy–2–iodo–α–D–talopyranosyl groups", pp. 157–159.

C.A. 97:6734s. Nitrosourea derivatives.

Thiem, Liebigs Ann. Chem. 1985, "Untersuchungen aur Darstellung von Desoxyzuker–Steroidglysosiden", pp. 2135–2150.

Steinkellner, ORTHOMolecular (1989), "Tumosteron Behandeling Van Kanker," pp. 206–211.

Stein Kellner unpublished chemical report.

Bolitt, J. Org. Chem. 1990, SS, "Direct Preparation of 2–Deoxy–D–glucopyranosides from Glucals without Ferrier Rearrangement", pp. 5812–5813.

Bolitt et al. *J. Org. Chem.* vol. 55 pp. 5812–5813, (1990).

Thiem et al. *Liebigs. Ann. Chem.* pp. 2135–2150, (1985).

*Primary Examiner*—Douglas W. Robinson
*Assistant Examiner*—Howard C. Lee
*Attorney, Agent, or Firm*—Young, MacFarlane & Wood

[57] ABSTRACT

Novel glycosides 7-ketosteryl di-O-acyl-pyranoside and 7-β-hydroxycholesteryl 2,3-dideoxy-α-D-erythro-hex-2-enopyranoside. The glycosides possess valuable pharmacological properties as a medicament. In particular, the cholesterol glycoside in vivo exhibits a selective cell-destructive activity on malignant cells which activity is substantially free of side effects on normal cells. The glycosides possess useful properties, especially pharmacological properties which are the same as the respective unglycosylated aglycon.

4 Claims, 8 Drawing Sheets

GLYCOSIDE COMPOUNDS AND PRODUCTION AND USE THEREOF

RELATED APPLICATIONS

This is a divisional of U.S. application Ser. No. 08/006,447 filed Jan. 21, 1993, now abandoned, which is a continuation-in-part of U.S. application Ser. No. 815,691 filed Jan. 24, 1992, now abandoned, which is a continuation-in-part of U.S. Ser. No. 733,915 filed Jul. 22, 1991, now abandoned, which is a continuation-in-part of U.S. application Ser. No. 644,002 filed Jan. 22, 1991, now U.S. Pat. No. 5,278,296.

FIELD OF THE INVENTION

The invention importantly relates to the glycoside compounds of diverse application having desired properties including pharmacodynamic properties; and to medicaments containing the compounds.

One object of the present invention is to provide glycosides as therapeutically-active agents. Still another object is to provide glycosides having utility and useful properties, especially pharmacological properties as detailed and referenced herein, for control of disease, especially for the treatment of certain cancer conditions.

It has been surprisingly found according to the invention that an aglycon compound—in a preferred embodiment, a hydroxy-steroid cholesterol can be reacted in one step with a glycosidic vinyl ether 3,4,6-tri-O-acyl-D-glucal of formula

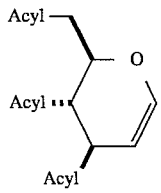

where Acyl is a lower acyl group, preferably a $C_{1-4}$ acyl group, in the presence of molecular halogen as a catalyst, such as iodine $I_2$, chlorine $Cl_2$, bromine $Br_2$ and fluorine $F_2$, preferably iodine, to provide the corresponding glycoside in high yield. Thus there is no need for expensive and/or toxic reagents in this reaction step. Further, as a preferred aspect of the invention, a steroidal glycoside—a 3-β-ol cholesterol pyranoside which is 7-β-hydroxycholesteryl-2,3-dideoxy-α-D-erythro-hex-2-enopyranoside (FIGS. 6 and 7 herein), obtainable by this method—has been found to be applicable as a pharmacologically active agent for use as a medicament, especially as an anti-neoplastic agent. For convenience in describing the invention, the term 4,6-di-O-acyl (or acetyl) -2,3-dideoxy-α-D-erythro-hex-2-enopyranoside will sometimes be referred to herein simply as DDH pyranoside.

BRIEF DESCRIPTION OF THE DRAWINGS

In the accompanying drawings with reference to preferred examples of the invention.

SUMMARY OF THE INVENTION

Cholesterol glycosides other than the above cholesterol glycoside produced according to the invention have the same utility and useful properties and art-recognized dosage regimens with the possible enhancement of bioavailability, e.g., at cell membranes, due to the presence of the sugar residue.

The steps of the glycosylation method and related oxidation and reduction methods employing the starting material cholesterol are as follows:

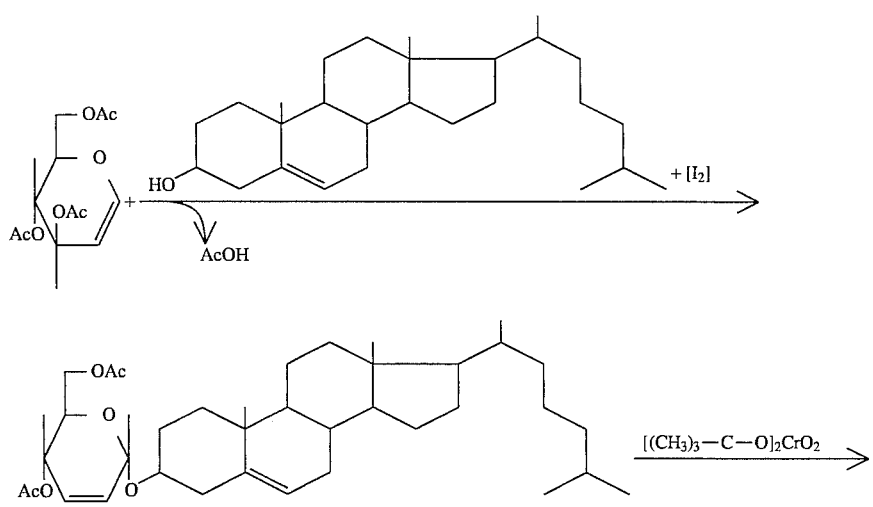

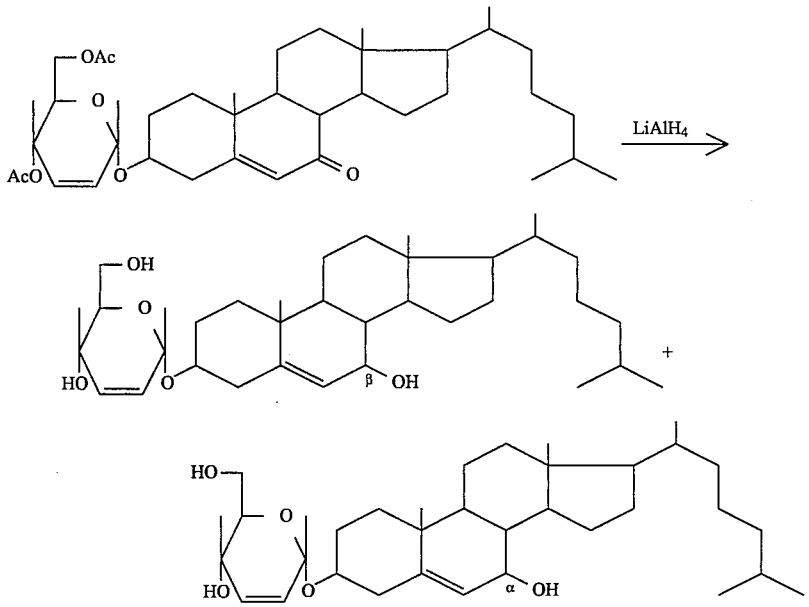

In another method aspect of the invention, the steryl DDH pyranoside product obtained by the glycosylation method can be converted by oxidation of the steroid part into an α-glycosylated 7-keto-sterol such as α-glycosylated 7-ketocholesterol. The oxidation is accomplished with an oxidizing agent, which preferably contains chromium, with pyridine-chromium trioxide $(C_5H_5N)_2CrO_3$ or pyridine-chlorochromate $(C_5H_5NHCrO_3)Cl$ being preferred and t-butyl chromate being especially preferred. The inert glycosidic double bond between $C_2$=$C_3$ thereby remains intact as it is shielded by the $C_4$, $C_6$ acyl (e.g., acetyl) groups. The reduction of this 7-ketone with a suitable reducing agent, preferably a complex metal hydride, such as one or more of $LiAlH_4$, $NaBH_4$, and $KBH_4$, more preferably $LiAlH_4$, provides 7β-hydroxycholesteryl 2,3-dideoxy-α-D-erythro-hex-2-enopyranoside (7β-OHC DDH pyranoside) of formula

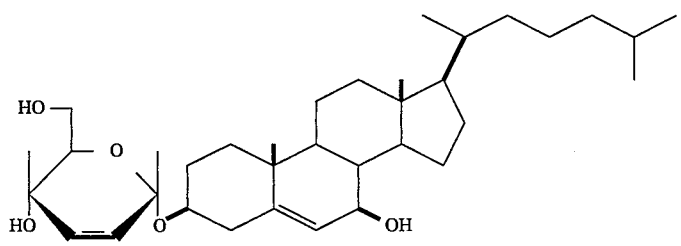

which like cholesterol is systemically biocompatible. The product is obtained after workup of the reaction mixture, e.g. by chromatographic separation of the $C_7$ β-hydroxy isomer from the $C_7$ α-hydroxy isomer, in a suitable solvent mixture, preferably a mixture comprising dichloromethane: acetone preferably in 1:1 mixture.

Figure 8:
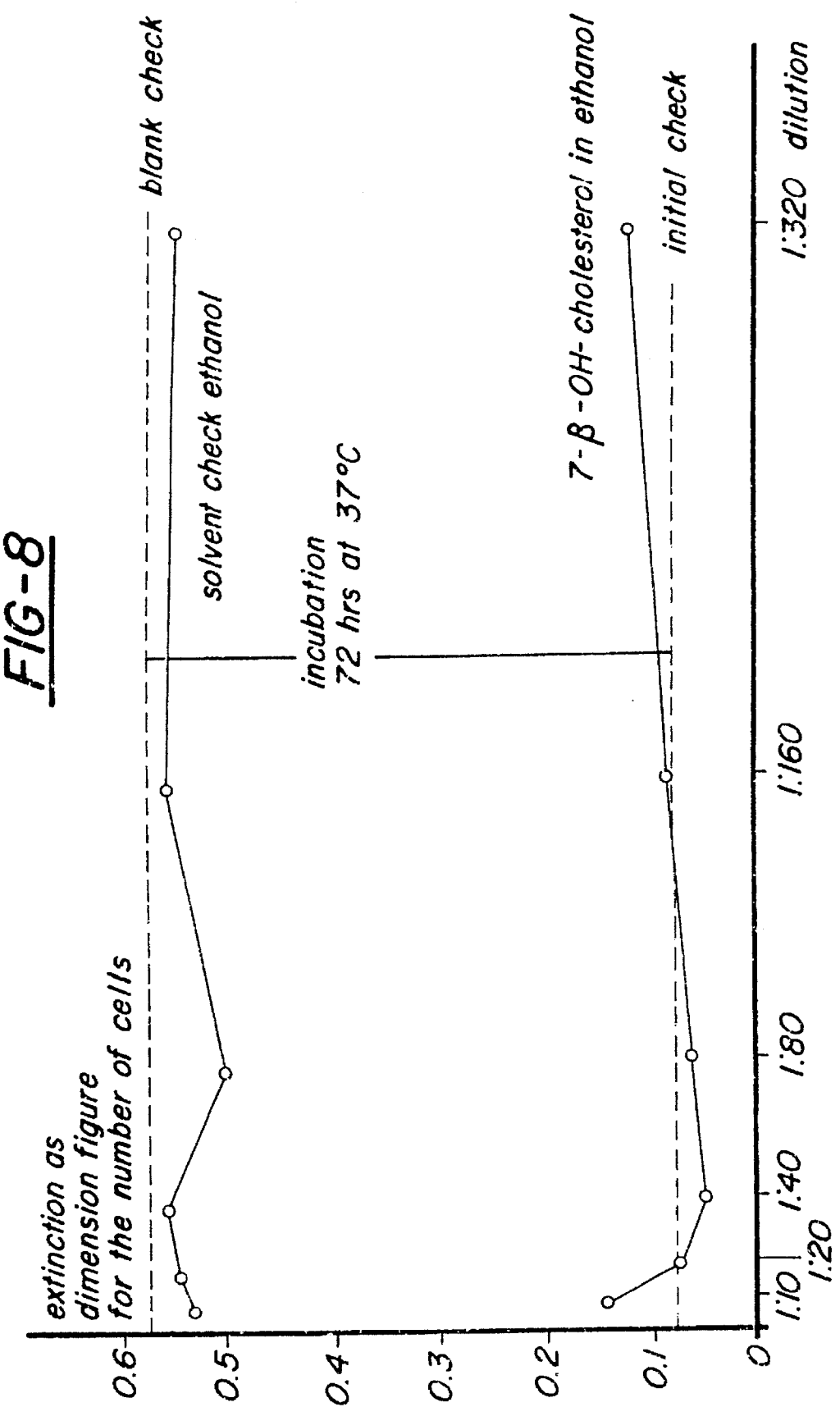
FIG. 8 is a plot showing the tumor cell growth inhibition by selected concentrations of 7β-OH cholesterol in K-562 cell culture fluid: 1/10 (0.4 mg/ml culture fluid; 0.9% ethanol present in culture), 1/80 (0.03 mg/ml culture fluid; 0.10% ethanol present), and 1/320 (0.007 mg/ml culture fluid; 0.030% ethanol present).

In a preferred aspect, the invention comprises the novel pyranoside compounds having the above formulas. The novel 7β-hydroxycholesterol DDH pyranoside in particular and its 7-keto precursor possess valuable pharmacological properties. These compounds are equivalent in this respect to the related aglycon 7β-OH cholesterol (7β-OHC) as the bishemisuccinate colamine salt which at low parenteral dosage has been shown in clinical studies to selectively inhibit the proliferative phase growth of cancer cells without substantial side effects, as reported in "Clinical Studies" by Dr. Steinkellner, Ortho Moleculair, No. 5 (1989) pp. 206–11, incorporated herewith by reference. The mentioned 7β-OHC salt also exhibits normalizing effects such as a drive-enhancing (stimulating) activity as well as a tranquilizing activity. The aglycon or steroidal moiety, which is 7β-hydroxycholesterol also known as $delta^5$-cholesten-3β,7β-diol, and its 7-keto analog are endogenous steroids of the thymus gland, being native signal substances of the cellular immune response. The aglycon compound 7β-hydroxycholesterol previously has been successfully employed as indicated in the treatment (free of side effects) of cancer diseases of several phenotypes. For example, a preferred parenteral dosage regimen in treating the proliferative phase growth of the kind described, allowing for ethical considerations and practices exercised in the clinician's judgment, calls for administration of about 10 to about 40 mg. of 7β-OHC DDH pyranoside per 70 Kg. of body weight, once a day or less often while analysis is made of tumor markers such as CEA, TPA, etc. so that the dosage can be adjusted from time to time to normalize the tumor marker level. Whereas the alpha-isomer, $delta^5$-cholesten-3β,7α-diol, is formed in the liver as the first degradation product of cholesterol and possesses no physiological activity, the beta-isomer, $delta^5$-cholesten-3β,7β-diol (as well as its 7-keto analog), is formed in the thymus gland of all mammals as a universal signal substance of the mammalian immune defense. It owes its activity, which is solely directed to malignant cell surfaces, to the fact that it is bound unspecifically by LDL (low density lipoproteins). The lipoproteins serve both for the essential transport of cholesterol into the interior of the cell and for the construction of the cell membranes. The beta-isomer also owes its activity to the fact that it is transferred by the lipoproteins, presumably via the NK-cells (natural killer cells) onto the cell membranes of deviated tissue, particularly onto cancerous tissue. As the receptors of LDL on the surface of cancer cells are degeneratively modified, having undergone a modification of their spatial structure in contrast to normal soma cells, the 7β-hydroxy-cholesterol effects a blocking of the receptors modified in this way. This is analogous to the plugging of a bottle, wherein the cancer cell is cut off from the supply of the vital cholesterol. Hence it follows that an osmotic excess pressure builds up in the interior of the cancer cell, finally leading to the colloid-osmotic induced rupture of the cancer cell. The cytoplasma of the cancer cell is then forced out. Thus the cancer cell ceases to exist (FIG. 8).

The cytolytic event, lasting only for about 8 to 10 minutes, has been investigated microscopically and recorded by Alex Matter [Microcinematographic and electron microscope analysis of target cell lysis induced by cytotoxic T lymphocytes, *Immunology* 36, 179–190 (1979)]. No statement concerning the chemical nature of the body's own active substance is made.

The 7-hydroxy- and 7-ketocholesterols are described respectively as being useful as an immunoregulatory agent or antiphlogistic agent (U.S. Pat. No. 4,157,391, incorporated herewith by reference). Water soluble cholesterol salts, useful as standards for the determination of cholesterol in biological fluids, are also known from U.S. Pat. No. 3,859,047. These are the morpholine, the cyclohexylamine, and the tris (hydroxymethyl) aminomethane salts of cholesteryl-hemisuccinate.

The novel cholesterol and precursor compounds of the invention can be used in the form of pharmaceutical preparations comprising each such compound in a pharmacogically effective amount in admixture with a pharmaceutically acceptable carrier which may be conventional per se. These preparations may be formulated by well known procedures. In these respects, see for example *Remington's Pharmaceutical Sciences*, Chapter 43, 14th Ed., Mack Publishing Co., Easton, Pa. 18042, USA. These preparations can be administered in any suitable way such as orally, e.g. in the form of tablets, dragees, gelatin capsules, soft capsules, solutions, emulsions or suspensions or parenterally, e.g. in the form of injectable solutions at suitable pH, e.g. ca. 7.5, or topically, e.g. in the form of a cream.

The carriers mentioned above may constitute pharmaceutically inert inorganic or organic materials. Examples of carriers for tablets, capsules and hard gelatine capsules include lactose, maize-starch or derivatives thereof, talcum, stearic acid or salts thereof. Examples of carrier for soft gelatine capsules include vegetable oils, waxes, fats, semisolid and liquid polyols. Examples of carriers for the manufacture of solutions or syrups include water, ethanol, propylene glycol, saccharose, invert sugar and glucose. Examples of carriers for injectable solutions include water, ethanol, polyols, propylene glycol, glycerol and vegetable oils. The pharmaceutical preparations may also comprise conventional pharmaceutical adjuvants such as preservatives, solubilizers, stabilizers, humectants, emulsifiers, sweetening agents, dyes or scents, salts (e.g., to modify the osmotic pressure), buffers, coating agents or antioxidants. They may also comprise at least one other systemically biocompatible and therapeutically valuable ingredient in a biochemically effective amount, including an antioxidant such as tocoquinones (tocopherols), glutathione, cysteine, ascorbic acid sodium salt, methionine, and the like.

The pharmaceutical preparations may be manufactured by admixing the compound according to this invention, if desired in combination with other therapeutically valuable substances, with an acceptable pharmaceutical carrier and, if desired, with a pharmaceutical adjuvant, and transforming the admixture into the desired form for administration.

The invention and the best mode for practicing the same are illustrated by the following examples.

EXAMPLE 1

Preparation of Cholesteryl 4,6-Di-O-acetyl-2,3-dideoxy-α-D-erythro-hex-2-enopyranoside

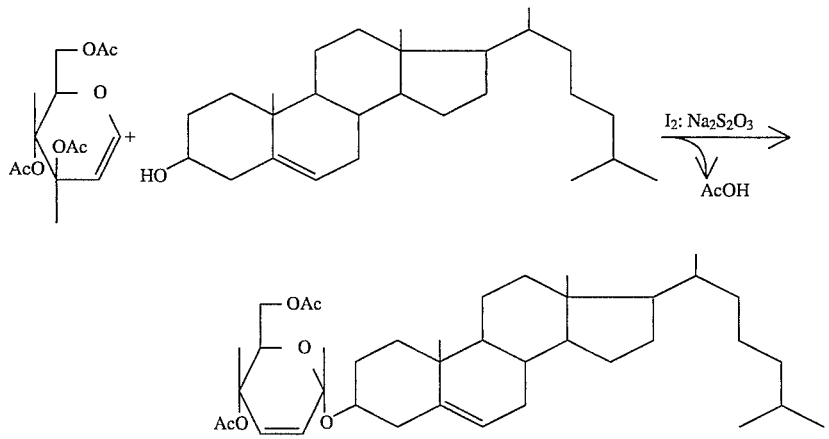

Figure 1:
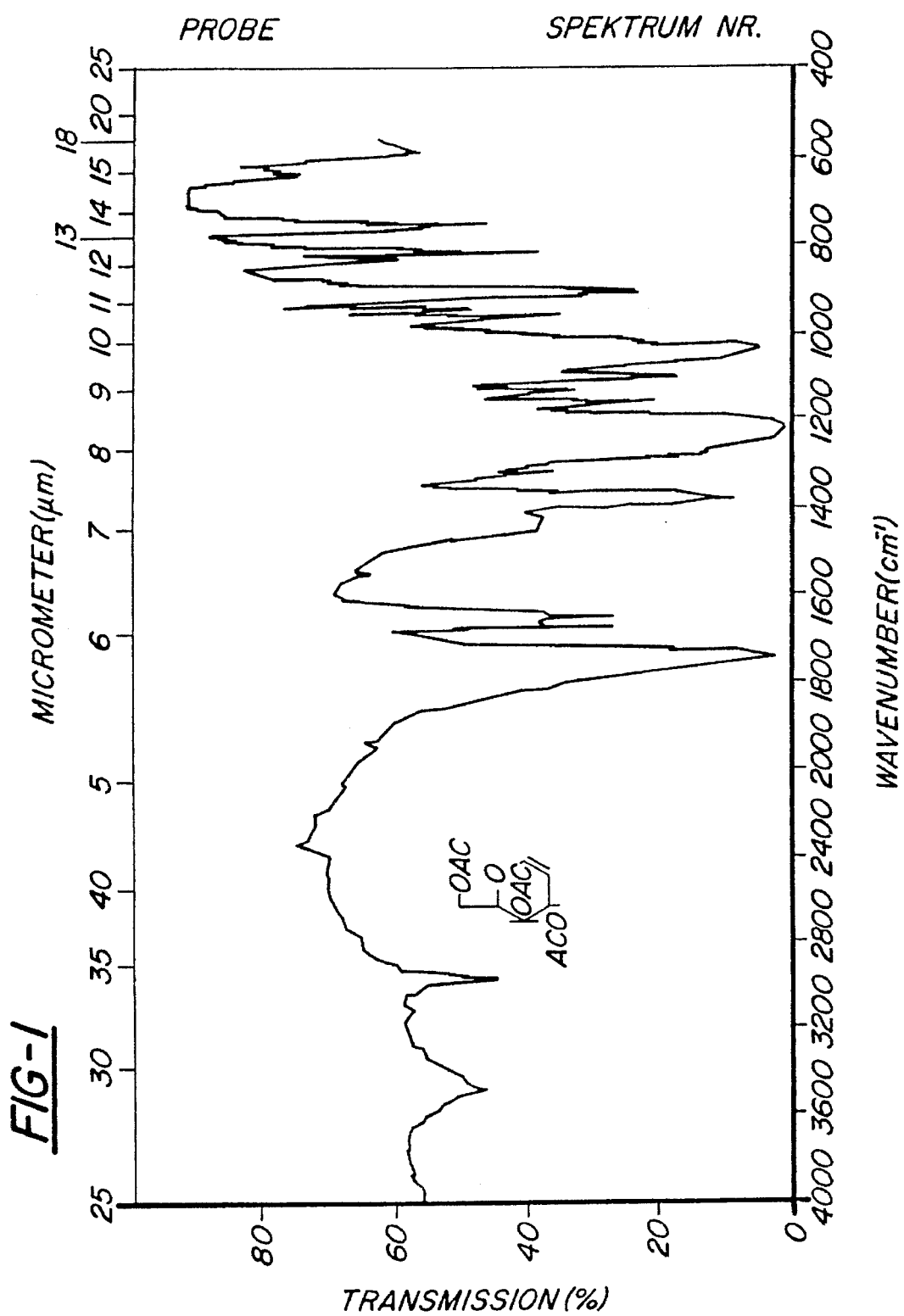
FIG. 1 is an infrared spectrum of the glucal used in the reaction of Example 1.

5.0 g (=0.02 mole) molecular iodine were dissolved with stirring in 300 ml benzene in a 2-litre three-necked flask fitted with stirrer, reflux condenser and thermometer. To the wine-red solution thus obtained was added the solution of 27.2 g (=0.10 mole) 3,4,6-tri-O-acetyl-D-glucal and 38.6 g (=0.10 mole) cholesterol (delta$^5$-cholesten-3β-ol) in 700 ml of benzene. In the course of 2 hours the mixture was heated to 70°–75° C. The reaction was monitored by IR-spectroscopy; it was terminated only when the peak of the glucal at 1650 cm$^{-1}$ (FIG. 1) had disappeared. The red color of the reaction solution is not significant. After removal of the flask heater the reaction solution is rapidly cooled in a water-bath to about 20°–30° C. After transfer into a 2-litre separatory funnel the cooled wine-red reaction solution was thoroughly shaken until complete discoloration with 500 ml+10% of 0.1N=12.5 g+10%=13.8 g aqueous solution of $Na_2S_2O_3$, washed twice with water, treated with activated carbon, dried over anhydrous $Na_2SO_4$ and the solvent distilled off, finally in vacuo.

Figure 2:
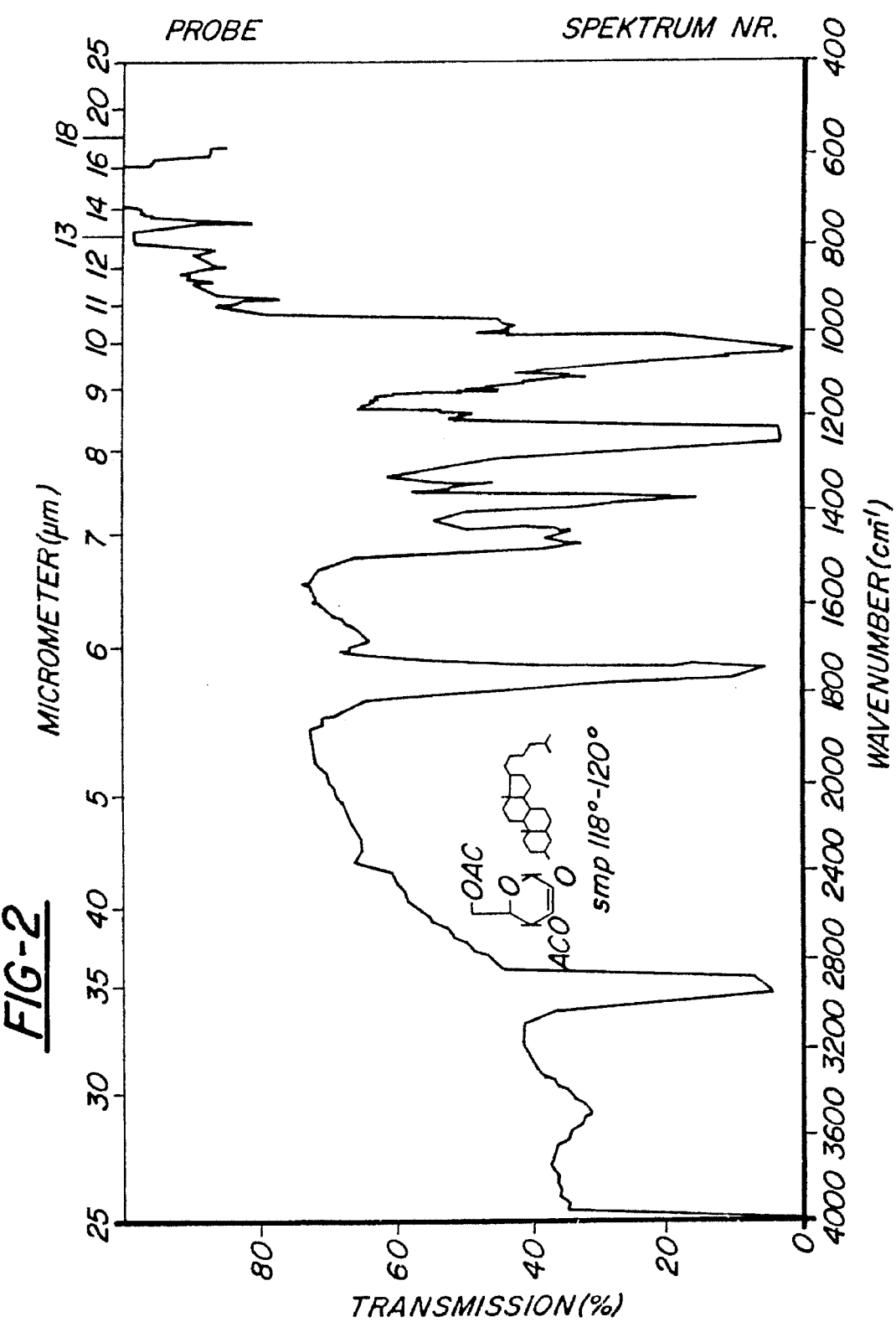
FIG. 2 is an infrared spectrum of the glycosylation product of Example 1.
Figure 3:
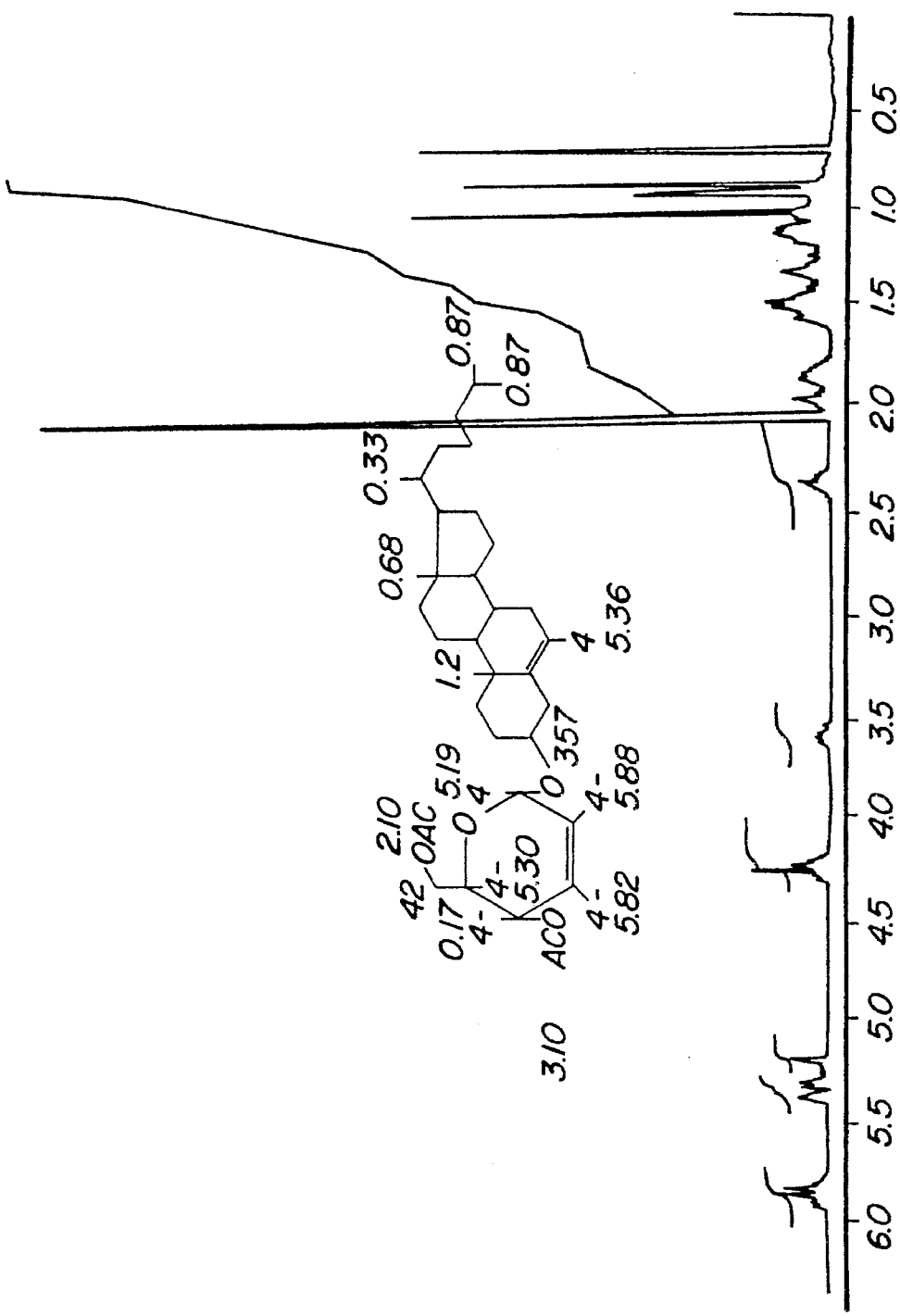
FIG. 3 is an NMR spectrum of the same glycosylation product of Example 1.

Crude yield: 58.3 g (=97.4% th.) The product, cholesteryl 4,6-di-O-acetyl-2,3-dideoxy-α-D-erythro-hex-2-enopyranoside, is recrystallized from 2 litres of $CH_3OH$. Yield: 56.95 g (=95.1% th.) Mp: 118°–120° C. IR-spectrum: FIG. 2 NMR-spectrum: FIG. 3

EXAMPLE 2

Preparation of 7-ketocholesteryl 4,6-Di-O-acetyl-2,3-dideoxy-α-D-erythro-hex-2-enopyranoside with activated carbon. After concentration in vacuo, the straw-yellow residue was dissolved in 25 ml of a mixture consisting of cyclohexane 40 : ethyl acetate 10 : chloroform 1 and chromatographed on a silica gel column (diameter 2.5 cm; height 25 cm), charged with 60 g of silica gel 40 (Merck Article 10180) and the same solvent mixture.

Figure 4:
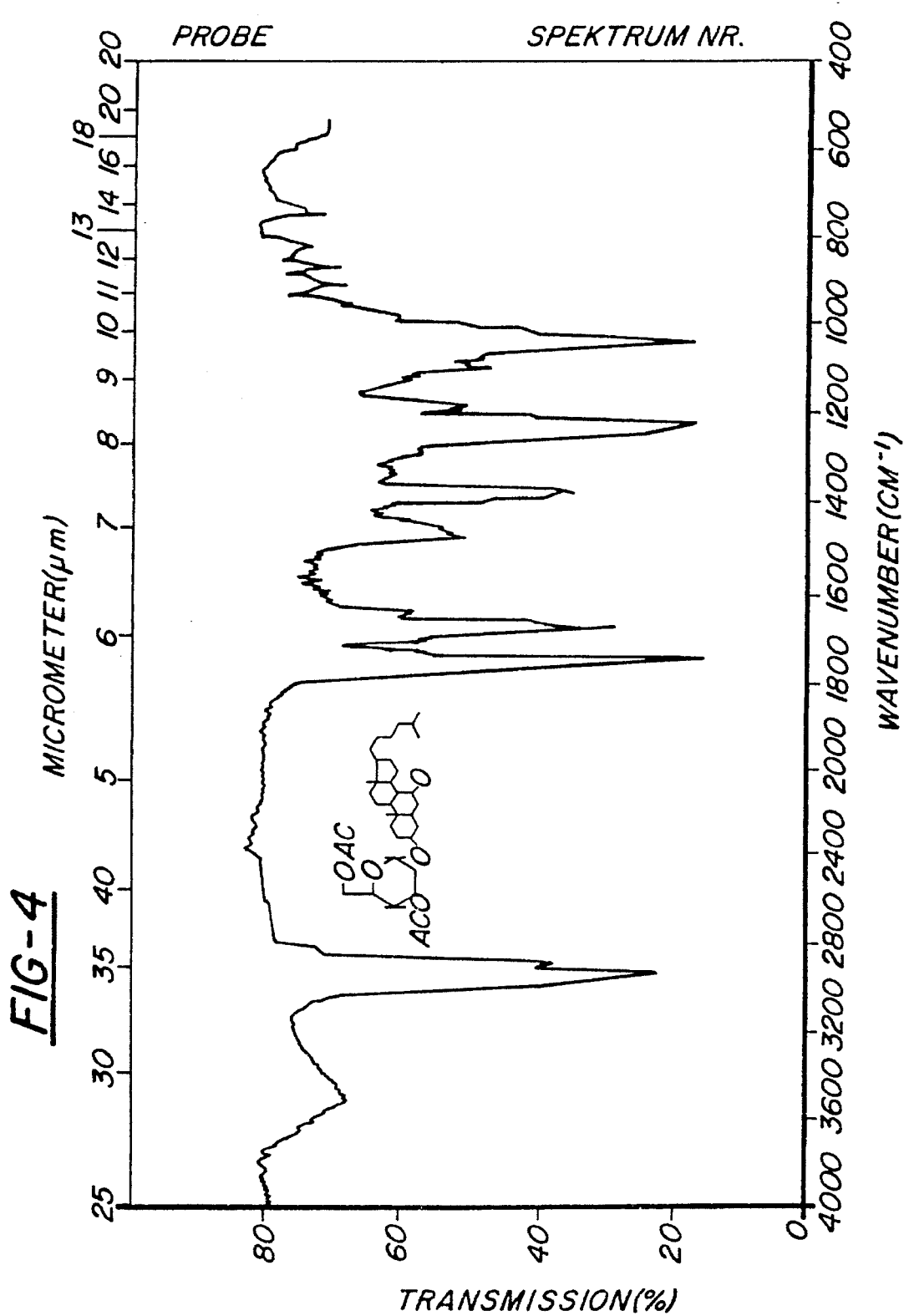
FIGS. 4 and 5 are the IR-spectrum and the NMR-spectrum, respectively of the ketone product of Example 2.
Figure 5:
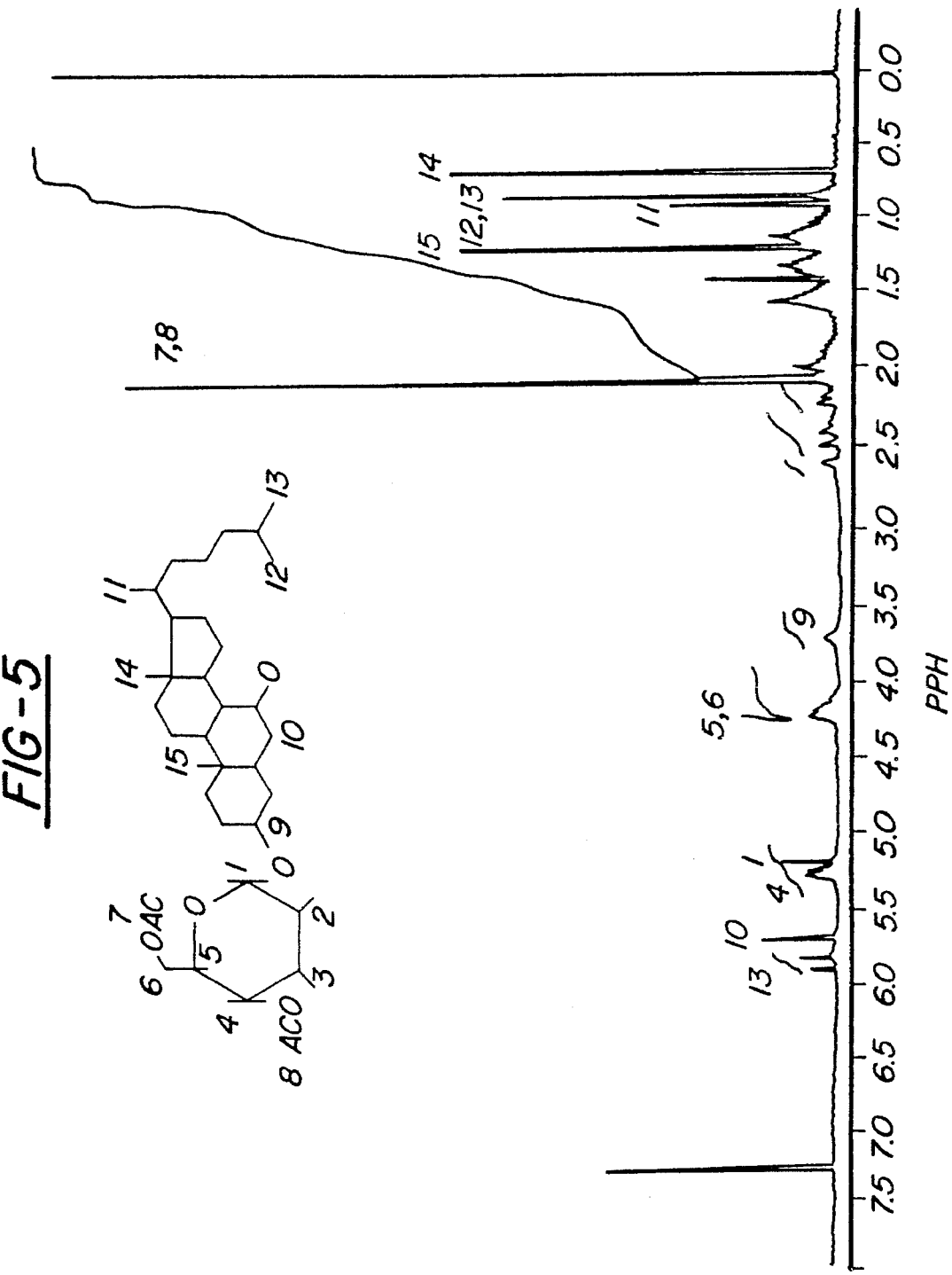

Yield: Fraction 1: 1.8 g (=30.1% of theory) unchanged starting material. Fraction: 2: 4.2 g (=68.5% of theory) 7-keto-compound Mp: 113°–115° C. IR-spectrum: FIG. 4 NMR-spectrum: FIG. 5
Annex:
Preparation of t-butyl chromate In a 500 ml beaker, 187.2 g (=2.5 mole) t-butanol of mp 24.5° C. were warmed to 28° C. and melted. To this melt, 74 g (=0.74 mole) of $CrO_3$ were added by using a thermometer as a stirring bar. In order to keep the reaction temperature

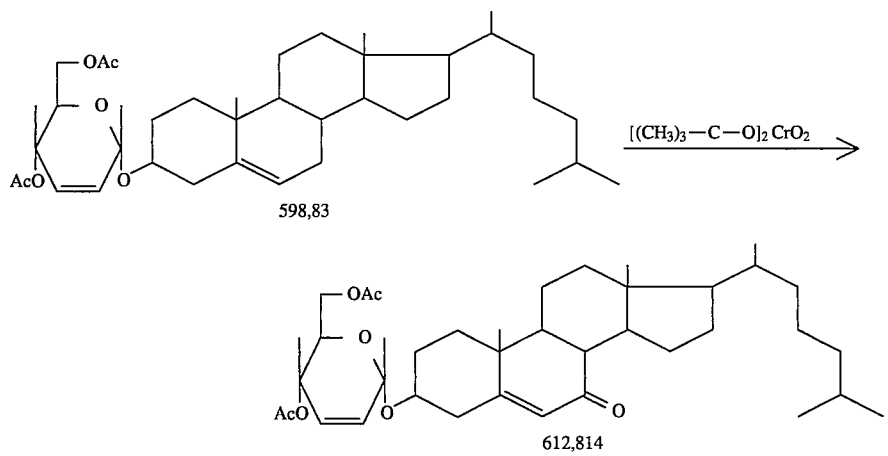

In a 250 ml three-necked flask fitted with reflux condensor, dropping funnel, thermometer and magnetic stirrer 6.00 g (=0.01 mole) of the unsaturated glycoside title product from Example 1 of mp 118°–120° C. were dissolved in 45 ml of $CCl_4$ and heated to boiling (80° C.). In the course of 30 minutes a mixture of 10 ml $Ac_2O$ (acetic anhydride) and 40 ml t-butyl chromate solution, prepared according to the Annex, was slowly added dropwise to the boiling solution and stirred for another 10 hours at the boiling point. After cooling, a solution of 6.0 g oxalic acid in 60 ml water was added dropwise in the course of 45 minutes at 5° C. to 10° C. in an ice-bath followed by 4.2 g solid oxalic acid. Stirring was then continued for another 2 hours. Thereafter separation took place in the separating funnel, the upper dark aqueous phase being extracted twice with $CCl_4$, the combined $CCl_4$-solutions extracted with water, saturated solution of $NaHCO_3$ and then with water again, in this order, and dried over $Na_2SO_4$. Finally the solution was decolorized below 30° C. occasional cooling with ice-water was necessary. The liquid reaction product was diluted in a separating funnel with 520 ml of $CCl_4$ and left to stand overnight. This standing is important to allow clarification of the solution. The following morning, the upper dark layer was separated. The clear $CCl_4$-solution was dried with 50 g of anhydrous $Na_2SO_4$, filtered and the $Na_2SO_4$ washed with 320 ml of $CCl_4$. Thereafter, the combined $CCl_4$-solutions were concentrated to 400 ml in vacuo in a water-bath at a temperature of 40° C. to 45° C., wherein excess t-butanol and $CCl_4$ were both distilled azeotropically. The solution thus obtained is relatively storage stable as it may be kept unchanged in the refrigerator at −1° C. for at least one month.

EXAMPLE 3

Preparation of 7-β-Hydroxycholestery 2,3-Dideoxy-α-D-erythro-hex-2-enopyranoside

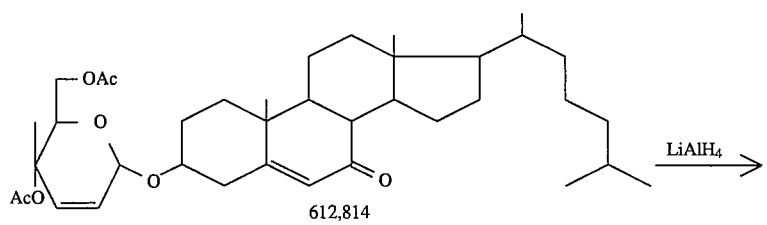

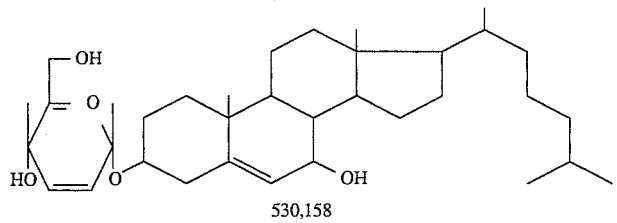

530,158

6.13 g (=0.01 mole) of pure compound from Example 2 with mp 113°–115° C. were dissolved by heating in 100 ml peroxide-free ether which has been dried with metallic sodium and cooled to room temperature. A solution of 0.8–1.0 g (=0. 021 mole) $LiAl_4$ in 100 ml absolute ether was added to a 500 ml three-necked flask with magnetic stirrer, reflux condensor and thermometer. The ethereal solution of the unsaturated aceto-7-keto-glucoside was then added dropwise with sufficient stirring to assure that the reaction temperature did not substantially exceed 20° C. After addition had been terminated, which may take up to two hours, stirring was continued for another two hours.

Afterwards, the reaction mixture was cooled in ice-water and treated drop by drop with $H_2O$ until all $H_2O$ (conducted to the outlet of the hood by means of a tube) had evolved. $H_2O$-consumption was about 5.0 ml. On a larger scale, the use of $CH_3COOC_2H_5$ is recommended. In order to dissolve the $LiAlO_2$ formed, the solution was stirred with 16 ml of 10% $H_2SO_4$ and, after transfer to a 500-ml separating funnel, diluted with 100 ml of ether and shaken thoroughly. Thereby, the reaction product, comprising a mixture of the title 7β-OH compound and its 7α-OH isomer, which has separated as crystals, goes completely into solution. The separated acidic aqueous solution was extracted once with ether and the combined ethereal solution was washed with 100 ml of a saturated NaCl-solution in two portions of 50 ml each. After drying over anhydrous $Na_2SO_4$, the filtrate was kept in the refrigerator at −1° C. for nine hours. The crystals thus obtained are collected by suction over a G4-suction filter and weighed.

Crude yield: 5.10 g (=96.23% of theory) Mp: 165°–167° C.

The product comprising a mixture of the title 7β-OH compound and its 7α-OH isomer was dissolved in 25 ml of dioxane (or THF) by heating and the resulting solution was chromatographed on a column of silica gel (diameter 5.0 cm; height 70 cm) charged with 300 g of silica gel 40 (Merck Article 10180) using a solvent mixture consisting of dichloromethane 1: acetone 1.

Figure 6:
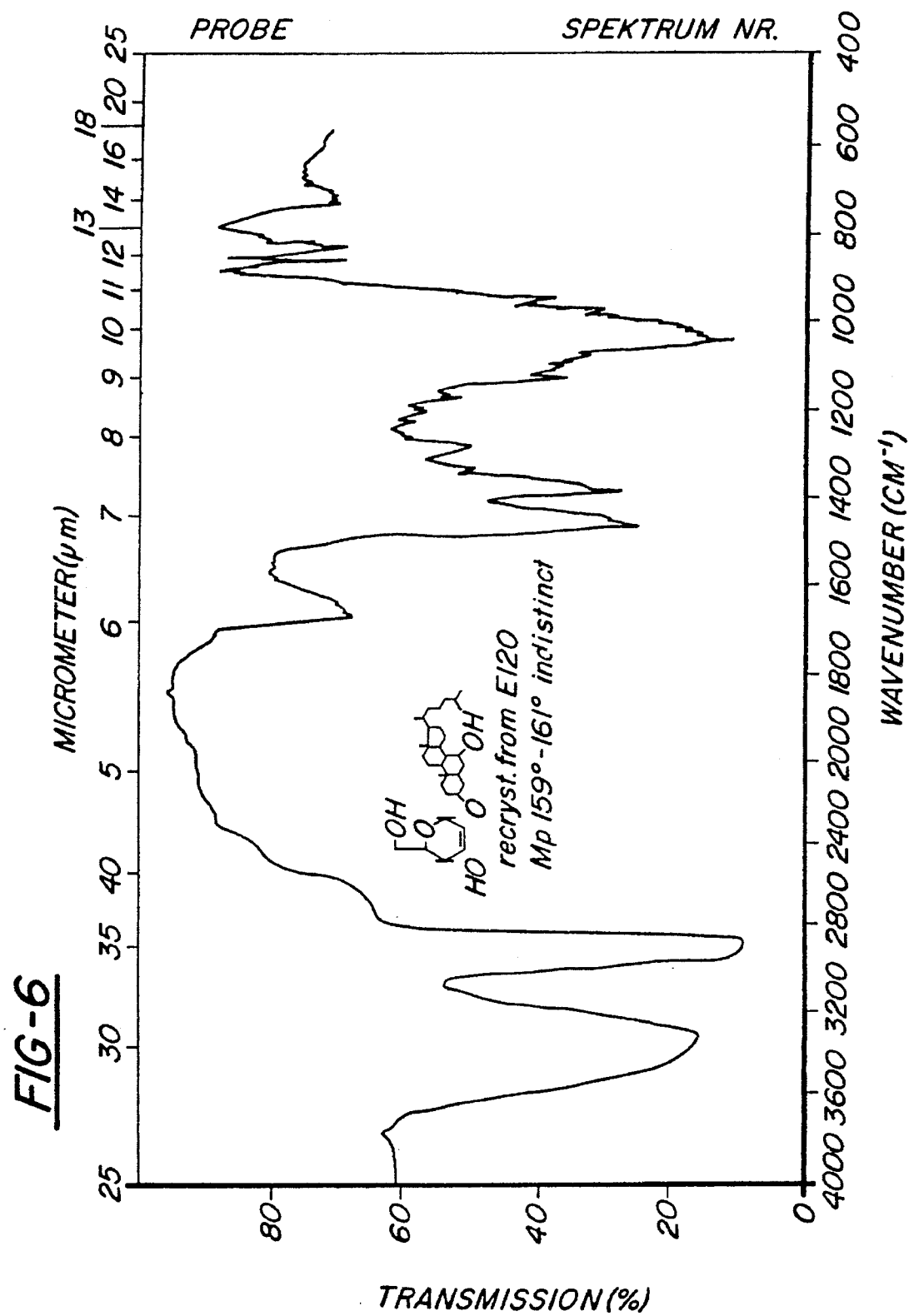
FIGS. 6 and 7 are the IR-spectrum and the NMR-spectrum, respectively, of the 7β-OHC product of Example 3.
Figure 7:
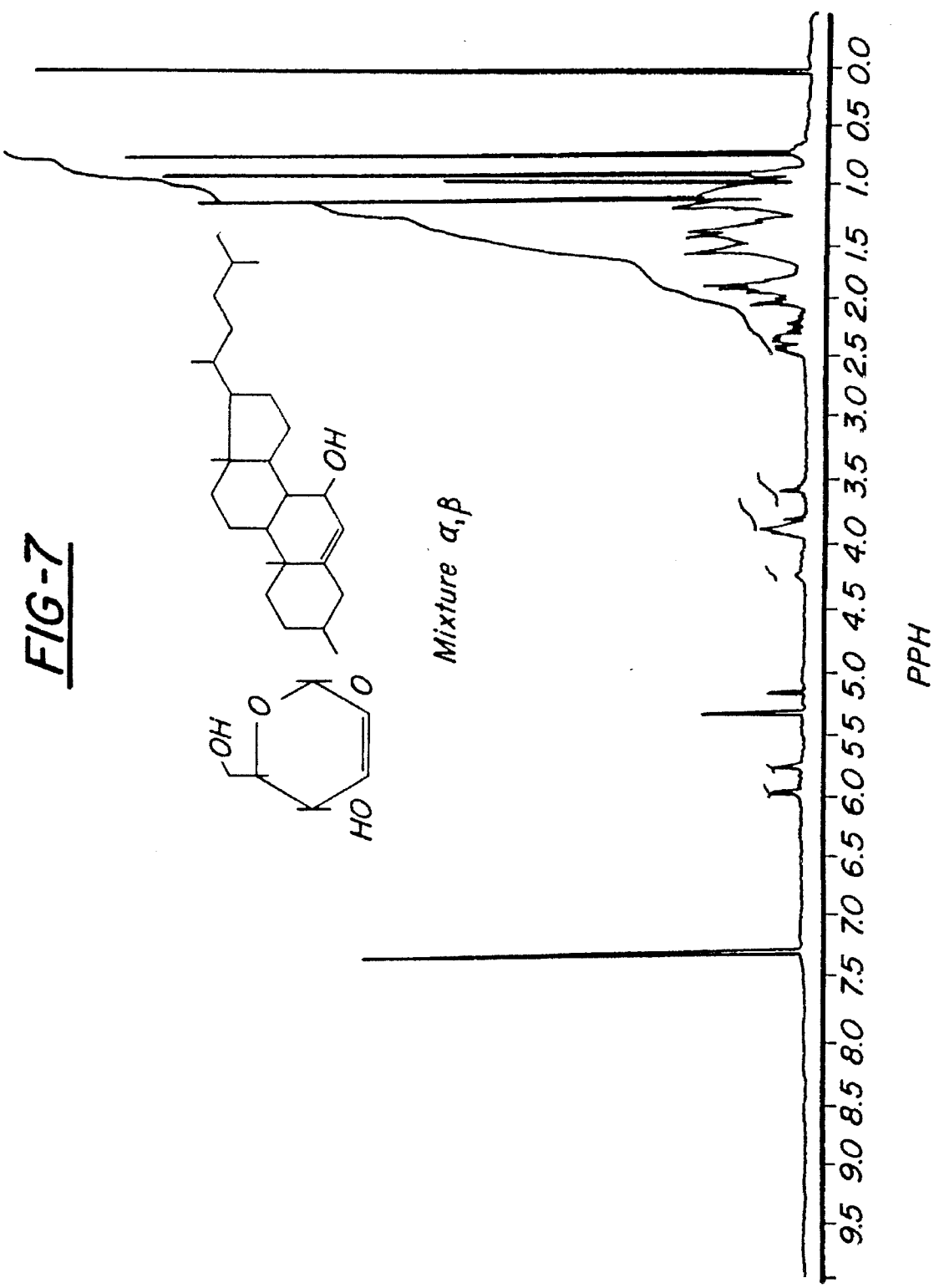

Yield: Fraction 1: 0.35 g (=6.8%) 7α-OH-compound, mp: 159°–161° C. Fraction 2: 4.60 g (=90.2%) 7α-OH-compound, top: 181°–183° C. IR-spectrum: FIG. 6 NMR-spectrum: FIG. 7

EXAMPLE 4

| Tablet | |
|---|---|
| 7-β-Hydroxycholesteryl 2,3-dideoxy-α-D-erythro-hex-2-enopyranoside | 200 g |
| Niacine amide | 600 g |
| Thiamine, HCl | 300 g |
| Pyridoxal phosphate | 200 g |
| Pyridoxal palmitate | 400 g |
| Magnesium citrate | 300 g |
| Magnesium stearate | 200 g |
| Milk sugar or corn starch | 400 g |

Combine the mixture in a planetary mixer and mix for 3 minutes. The mixture is milled and the total blend is drum rolled for 5 minutes. Compressed tablets of 260 mg of the total mix are formed with appropriate size punches, each tablet containing 20 mg. of the cholesteryl glycoside for oral administration.

EXAMPLE 5

| Suppository | | |
|---|---|---|
| a. | 7-β-Hydroxycholesteryl 2,3-dideoxy-α-D-erythro-hex-2-enopyranoside | 0.1 g |
| b. | Milk sugar | 1.0 g |
| c. | Aerosil | 0.2 g |
| d. | Suppository base, PEG (Stadinol) | 23.7 g |
| | | 25.0 g |

Melt the polyethylene glycol and mix ingredients a, b and c into the melt. Mold this total into appropriate suppositories. For adults; the mixture makes for 10 suppositories.

EXAMPLE 6

| Capsule | | |
|---|---|---|
| a. | 7-β-Hydroxycholesteryl 2,3-dideoxy-α-D-erythro-hex-2-enopyranoside | 5.0 mg |
| b. | Glutathione | 100.0 mg |
| c. | L-Cysteine | 30.0 mg |
| d. | Vitamin C | 200.0 mg |
| e. | Milk sugar | 40.0 mg |
| | | 365.0 mg |

Capsules of appropriate size are each filled with the mixed and blended ingredients to provide a capsule containing 5 mg of the cholesteryl glycoside.

EXAMPLE 7

| Salve | | |
|---|---|---|
| a. | 7-β-Hydroxycholesteryl 2,3-dideoxy-α-D-erythro-hex-2-enopyranoside | 1.0 g |
| b. | Procaine | 2.0 g |
| c. | Niacin | 5.0 g |
| d. | Ointment Base (Eucerin ®, Beiersdorf) | 92.0 g |
| | | 100.0 g |

Ingredients a), b) and c) are mixed in and blended with the ointment base which is subdivided for topical application of a unit dose of salve containing 10 mg of ingredient a).

EXAMPLE 8

Injectable

7-β-Hydroxycholesteryl 2,3-dideoxy-α-D-erythro-hex-2-enopyranoside (1.0 g) is dissolved in 30 ml ethanol with warming and stirred with 162 ml 1,2-propylene glycol. To the resulting clear solution there is added 8 ml water with mixing, and the solution is filtered and placed in ampoules and sealed. This provides 100 ampoules each containing 2 ml of injectable which in turn contains 10 mg of the active hydroxycholesteryl glycoside.

Having described the invention, the embodiments of the invention in which an exclusive property or privilege is claimed are defined as follows:

1. A 3β,7β-dihydroxysteryl 2,3-dideoxy-α-D-erythro-hex-2-enopyranoside compound of formula

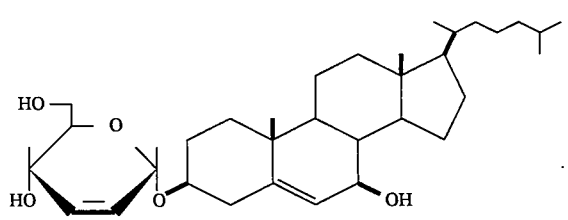

2. A 3β-hydroxy 7-ketosteryl 4,6-di-O-acyl-2,3-dideoxy-α-D-erythro-hex-2-enopyranoside of formula

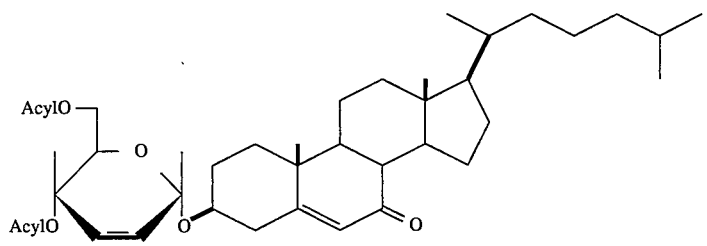

where Acyl is a lower acyl group.

3. A medicament for inhibiting the growth of neoplastic cells which comprises in pharmaceutically acceptable dosage form an effective neoplastic cell growth inhibiting amount of a 3β7β-dihydroxypyranoside of formula

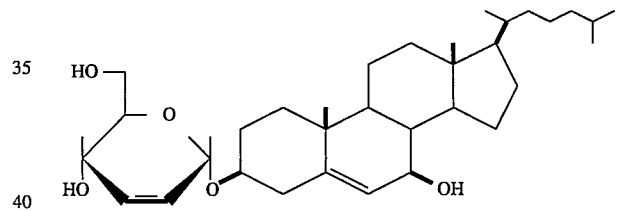

in a pharmaceutically acceptable carrier.

4. A medicament according to claim 3 comprising a liquid carrier selected from the group consisting of a) water, b) ethanol, c) propylene glycol, and a mixture of two or more of a), b) and c).

* * * * *

UNITED STATES PATENT AND TRADEMARK OFFICE
CERTIFICATE OF CORRECTION

PATENT NO. : 5,496,806
DATED : March 5, 1996
INVENTOR(S) : Klemke

It is certified that error appears in the above-indentified patent and that said Letters Patent is hereby corrected as shown below:

Column 9, line 52, delete "top" and insert --mp--;

Column 12, line 32, delete "$3\beta7\beta$" and insert -- $3\beta,7\beta$ --.

Signed and Sealed this

Sixth Day of August, 1996

Attest:

BRUCE LEHMAN

Attesting Officer    Commissioner of Patents and Trademarks